(12) United States Patent
Bora et al.

(10) Patent No.: US 7,964,557 B2
(45) Date of Patent: Jun. 21, 2011

US007964557B2

(54) INHIBITION OF WET TYPE AGE RELATED MACULAR DEGENERATION (AMD) BY ADIPONECTIN OR ACRP 30

(75) Inventors: Puran S. Bora, Little Rock, AR (US); Nalini S. Bora, Little Rock, AR (US); Henry J. Kaplan, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 411 days.

(21) Appl. No.: 11/910,188

(22) PCT Filed: Mar. 22, 2006

(86) PCT No.: PCT/US2006/011008
§ 371 (c)(1),
(2), (4) Date: Dec. 20, 2007

(87) PCT Pub. No.: WO2006/104964
PCT Pub. Date: Oct. 5, 2006

(65) Prior Publication Data
US 2008/0221030 A1    Sep. 11, 2008

Related U.S. Application Data

(60) Provisional application No. 60/665,702, filed on Mar. 28, 2005.

(51) Int. Cl.
*A61K 38/00* (2006.01)
*A61K 47/00* (2006.01)
*A61K 49/00* (2006.01)
*A61P 27/02* (2006.01)
*C07K 7/00* (2006.01)

(52) U.S. Cl. ......... 514/1.1; 514/1.2; 514/1.3; 514/13.3; 514/20.8; 424/9.34; 530/300

(58) Field of Classification Search ................. None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis et al. |
| 4,800,159 | A | 1/1989 | Mullis et al. |
| 5,869,330 | A | 2/1999 | Scherer et al. |
| 6,344,441 | B1 * | 2/2002 | Bihain et al. ............. 514/12 |
| 6,448,221 | B1 | 9/2002 | Sheppard et al. |

FOREIGN PATENT DOCUMENTS

| | | |
|---|---|---|
| WO | WO 03/055916 | 7/2003 |
| WO | WO 04/056861 | 7/2004 |

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Accession NCBI No. AAK58902 (2001).
Accession NCBI No. AAK92202 (2001).
Accession NCBI No. AAL09702 (2001).
Accession NCBI No. BAB22597 (2006).
Accession NCBI No. NP_004788 (2008).
Ausubel et al. (Eds.) (2008) *Current Protocols in Molecular Biology*, Greene Publishing and Wiley Interscience, New York—(Table of Contents only).
Berg et al. (2002) *Trends Endocrinol. Metab.* 13, 84-89.
Bora et al. (2005) *J. Immunol.* 174:491-497.
Brakenhielm et al. (2004) *Proc. Natl Acad. Sci. USA.* 101: 2476-2481.
Campochiaro et al. (2000) 184:301-310.
Cao et al. (2001) *PNAS* 98:6390-6395.
D'Amore et al. (1994) *Invest. Opthalmol. Vis. Sci.* 35:3874-3879.
Espinosa-Heidmann et al. (2003) *Invest. Opthamol. Vis. Sci.* 44:3586-3592.
Fine et al.(2000) *N. Engl. J. Med.* 342:483-492.
Fischer (1983) *Meth. Enzymol.* 100:424-430.
Fruebis et al. (2001) *PNAS* 98:2005-2050.
Goodman and MacDonald (1979) *Meth. Enzymol.* 68:75-90.
Jackson et al. (1997) *FASEB J.* 1997 11:457-465.
Jain RK (2005) *Science* 307:58-62.
Liu et al. (2004) *Curr. Opin. Ophthalmol* 15:221-226.
Maeda et al. (2001) *Nat. Med.* 8:731-737.
Maeda et al. (1996) *BBRC* 221:286-28.
Matsubara et al. (2002) *J Clin Endocrinol Metab.* 87, 2764-2769.
Mousa et al. (2004) *Current Pharmaceutical Design* 10:1-9.
Nakano et al. (1996) *J. Biochem.* 120: 803-812.
Ouchi et al. (2004) *J. Biol. Chem.* 279:1304-9.
Pierce et al. (1995) *PNAS* 92:905-909.
Rose et al. (1996) *Clinical CancerResearch* 2:1751-1756.
Rose et al. (2004) *Obes. Rev.* 5:153-65. Sakurai et al. (2003) *Invest. Opthamol. Vis. Sci.* 44:3578-3585.
Sandri-Goldin et al. (1983) *Meth. Enzymol.* 101:402-411.
Scherer et al. (1995) *J. Biol. Chem.* 270:26746-26749.
Shibata et al. (2004) *J. Biol. Chem.* 279:28670-4.
Wei et al. (1983) *J. Biol. Chem.* 258:13006-13512).
Weyer et al. (2001) *J Clin Endocrinol Metab.* 86:1930-1935.
Xu et al. (2003) *J. Clin. Invest.* 112(1): 91-100.
Yamauchi et al. (2001) *Nat. Med.* 7:941-946.
Yi et al. (1997) *Graefe's Arch. Clin. Exp. Opthamol.* 235:313-319.
Yilmaz et al. (2004) *Eur. J. Endocrinol.* 151:135-140.

(Continued)

*Primary Examiner* — Chang-Yu Wang
(74) *Attorney, Agent, or Firm* — Greenlee Sullivan PC

(57) ABSTRACT

The present invention provides new methods of treating wet type of age related macular degeneration by administering adiponectin (APN) or a functional fragment derived therefrom. One of the pathological complications of age related macular degeneration (AMD) is choroidal angiogenesis or choroidal neovascularization (CNV). The inventors discovered that the level of APN expression is significantly lower in the choroids of the laser-induced mouse model of choroidal angiogenesis or choroidal neovascularization (CNV) than that of the control mice and that administration of recombinant adiponectin (rAPN) or a peptide derived from the globular domain of the intact APN protein to the mouse model of CNV reduced the size of CNV significantly. These studies are the first to demonstrate the inhibitory effect of adiponectin on choroidal angiogenesis and thus provide the basis for treating a condition or disease involving angiogenesis, particularly age related macular degeneration, with administration of adiponectin.

12 Claims, 6 Drawing Sheets

OTHER PUBLICATIONS

Yilmaz et al. (2004) *Eur. J. Endocrinol.* 152:233-240.
Yokota et al. (2000) *Blood* 96:1723.
Ferris et al. (1984) *Arch. Opthalmol.* 102:1640-1642.
Larionov, O.A. et al. (1982) *Genetika* 18(3):349-59—(English Abstract).
Maniatis et al. (1980) *Meth. Enzymol.* 65:299-305.
Metzger et al. (1988) *Nature*, 334: 31-36.
Saiki et al. (1985) *Science* 230:1350-1354.
Shortle, D. et al. (1981) *Annu. Rev. Genet.* 15:265-94.
Stupack et al. (2004) *Curr Top Dev Biol.* 64:207-238.

* cited by examiner

GAPDH APN 1 2 3 4

GAPDH VEGF 1 2 3 4

GAPDH ßFGF 1 2 3 4

(a)

(b)

1 2 3

FIG. 5
FIG. 6A
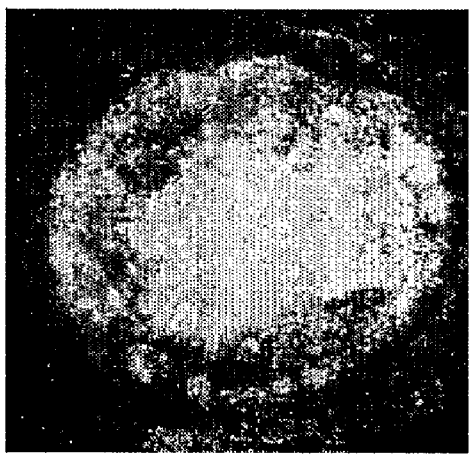
FIG. 6B
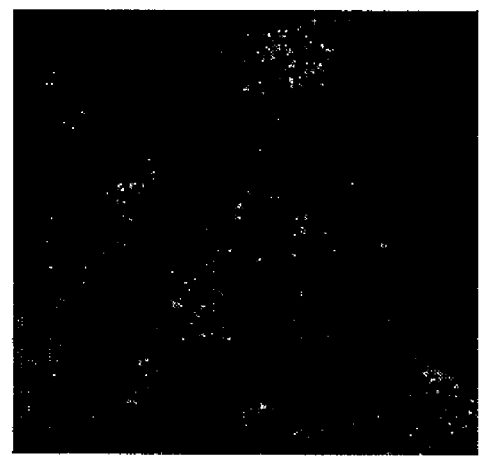
FIG. 6C
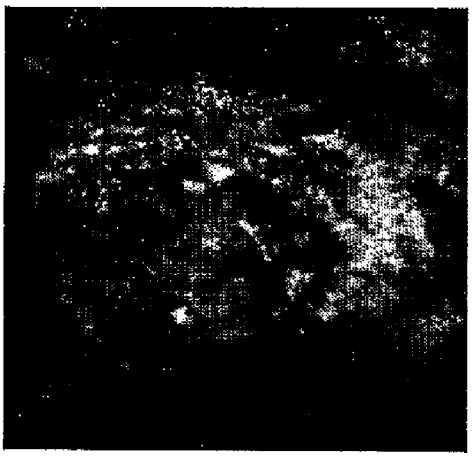
FIG. 6D
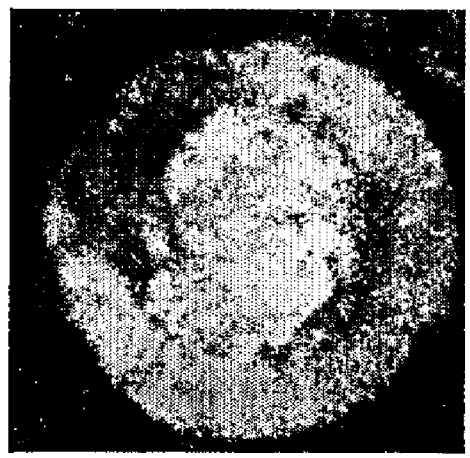

SEQUENCE LISTING

```
<160> NUMBER OF SEQ ID NOS: 14

<210> SEQ ID NO 1
<211> LENGTH: 18
<212> TYPE: PRT
<213> ORGANISM: Artificial sequence
<220> FEATURE:
<223> OTHER INFORMATION: Synthetic peptide

<400> SEQUENCE: 1

Leu Gln Val Tyr Gly Asp Gly Asp His Asn Gly Leu Tyr Ala Asp Asn
1               5                   10                  15

Val Asn

<210> SEQ ID NO 2
<211> LENGTH: 18
<212> TYPE: PRT
<213> ORGANISM: Artificial sequence
<220> FEATURE:
<223> OTHER INFORMATION: Synthetic peptide

<400> SEQUENCE: 2
```

```
Leu Gln Val Tyr Gly Glu Gly Glu Arg Asn Gly Leu Tyr Ala Asp Asn
1               5                   10                  15

Asp Asn

<210> SEQ ID NO 3
<211> LENGTH: 18
<212> TYPE: PRT
<213> ORGANISM: Artificial sequence
<220> FEATURE:
<223> OTHER INFORMATION: Synthetic peptide

<400> SEQUENCE: 3

Leu Gln Val Tyr Glu Gly Glu Asn His Asn Gly Val Tyr Ala Asp Asn
1               5                   10                  15

Val Asn

<210> SEQ ID NO 4
<211> LENGTH: 18
<212> TYPE: PRT
<213> ORGANISM: Artificial sequence
<220> FEATURE:
<223> OTHER INFORMATION: Synthetic peptide

<400> SEQUENCE: 4

Leu Gln Val Tyr Gly Glu Gly Glu Arg Asn Gly Leu Tyr Ala Asp Asn
1               5                   10                  15

Asp Asn

<210> SEQ ID NO 5
<211> LENGTH: 26
<212> TYPE: DNA
<213> ORGANISM: Artificial sequence
<220> FEATURE:
<223> OTHER INFORMATION: Synthetic nucleotide primer

<400> SEQUENCE: 5
tgaaggtcgg tgtgaacgga tttggc                                          26

<210> SEQ ID NO 6
<211> LENGTH: 24
<212> TYPE: DNA
<213> ORGANISM: Artificial sequence
<220> FEATURE:
<223> OTHER INFORMATION: Synthetic nucleotide primer

<400> SEQUENCE: 6
catgtaggcc atgaggtcca ccac                                            24

<210> SEQ ID NO 7
<211> LENGTH: 18
<212> TYPE: DNA
<213> ORGANISM: Artificial sequence
<220> FEATURE:
<223> OTHER INFORMATION: Synthetic nucleotide primer

<400> SEQUENCE: 7
gcgggctgcc tcgcagtc                                                   18

<210> SEQ ID NO 8
<211> LENGTH: 20
<212> TYPE: DNA
<213> ORGANISM: Artificial sequence
<220> FEATURE:
<223> OTHER INFORMATION: Synthetic nucleotide primer
```

```
<400> SEQUENCE: 8
tcaccgcctt ggcttgtcac                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic nucleotide primer

<400> SEQUENCE: 9
agcggctcta ctgcaagaac                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic nucleotide primer

<400> SEQUENCE: 10
tcgtttcagt gccacatacc                                              20

<210> SEQ ID NO 11
<211> LENGTH: 23
<212> TYPE: DNA
<213> ORGANISM: Artificial sequence
<220> FEATURE:
<223> OTHER INFORMATION: Synthetic nucleotide primer

<400> SEQUENCE: 11
ccaaagactt aacatctccc acc                                          23

<210> SEQ ID NO 12
<211> LENGTH: 21
<212> TYPE: DNA
<213> ORGANISM: Artificial sequence
<220> FEATURE:
<223> OTHER INFORMATION: Synthetic nucleotide primer

<400> SEQUENCE: 12
gttcgatctt gggcgtattt c                                            21

<210> SEQ ID NO 13
<211> LENGTH: 24
<212> TYPE: DNA
<213> ORGANISM: Artificial sequence
<220> FEATURE:
<223> OTHER INFORMATION: Synthetic nucleotide primer

<400> SEQUENCE: 13
atgggctatg ggtagttgca gtca                                         24

<210> SEQ ID NO 14
<211> LENGTH: 24
<212> TYPE: DNA
<213> ORGANISM: Artificial sequence
<220> FEATURE:
<223> OTHER INFORMATION: Synthetic nucleotide primer

<400> SEQUENCE: 14
tagcttcatg ctttgggtcc tcca                                         24
```

INHIBITION OF WET TYPE AGE RELATED MACULAR DEGENERATION (AMD) BY ADIPONECTIN OR ACRP 30

CROSS-REFERENCE TO RELATED APPLICATIONS

This application is the U.S. National Stage of International Application No. PCT/US2006/011008, filed Mar. 22, 2006 and published in English on Oct. 5, 2006 as WO 2006/104964 A2, which claims the benefit of U.S. Provisional Application 60/665,702, filed Mar. 28, 2005; all of which are hereby incorporated by reference in their entirety to the extent not inconsistent with the disclosure herein.

The present invention relates to methods of inhibiting choroidal angiogenesis or choroidal neovascularization. Specifically, the invention provides new methods of treating wet type age related macular degeneration (AMD) by employing adiponectin or a functional fragment derived therefrom.

BACKGROUND OF THE INVENTION

Angiogenesis is the process of blood vessel growth from pre-existing vasculatures. In recent years, angiogenesis has been elucidated as an important physiological phenomenon in proliferation and metastasis of various progressive solid cancers (Jain R K 2005 Science 307:58-62; Stupack et al. 2004 Curr Top Dev Biol. 64:207-238). Angiogenesis proceeds through multiple steps including, for example, 1) stimulation by vascular endothelial growth factor secreted from tumor cells; 2) disengagement of peritheliocyte or decomposition or digestion of extracellular matrix such as basal membrane; 3) migration and proliferation of vascular endothelial cells; 4) formation of tubules by the endothelial cells, formation of basal membrane, and maturation of blood vessel. In tumorous angiogenesis, the new vessels generated have the role of supplying oxygen and nutrient to tumors to accelerate their growth and serving as a route for infiltration and metastasis of tumor cells to other cells.

Age-related macular degeneration (AMD) is an angiogenesis-mediated ocular disorder in humans and is the leading cause of visual loss in individuals over age 55 (Ferris et al. 1984 Arch. Opthalmol. 102:1640-1642). There are two major clinical types of AMD: non-exudative (dry) type and exudative (wet) type. One of the pathological complications of age-related macular degeneration is choroidal angiogenesis or choroidal neovascularization (CNV). CNV is responsible for the sudden and disabling loss of central vision (Ferris et al. supra; Fine et al. 2000 N. Engl. J. Med. 342:483-492; Campochiaro et al. 2000 184:301-310).

CNV is a complex biological process and the pathogenesis of new choroidal vessel formation is not fully understood. Several factors such as inflammation (Campochiaro et al. supra; Jackson et al. 1997 FASEB J. 1997 11:457-465), ischemia (D'Amore at el. 1994 Invest Opthalmol. Vis. Sci. 35:3874-3879), and local production of angiogenic factors (Yi et al. 1997 Graefe's Arch. Clin. Exp. Opthalmol. 235:313-319; Pierce et al. 1995 PNAS 92:905-909) are thought to be important in the pathogenesis of CNV. A mouse model of laser-induced choroid neovascularization (Bora et al. 2005 J. Immunol. 174:491-497; Sakurai et al. 2003 Invest Opthamol. Vis. Sci. 44:3578-3585; Espinosa-Heidmann et al. 2003 Invest. Opthamol. Vis. Sci. 44:3586-3592) has been used to study the pathogenesis and to test potential therapeutics for AMD.

Adiponectin (APN), also called Acrp 30, adipoQ, or GBP28, is a plasma protein secreted from adipocytes and is shown to have structural similarities to C1q as well as to members of the tumor necrosis factor (TNF) superfamily. See Scherer et al. 1995 J. Biol. Chem. 270:26746-26749; Fruebis et al. 2001 PNAS 98:2005-2010; Hu et al. 1996 J. Biol. Chem. 271:10697-10703; Maeda et al. BBRC 1996 221:286-289; and Nakano et al. 1996 J. Biochem. 120: 803-812.

Adiponectin (APN) is composed of 244 amino acid residues containing a short noncollagenous N-terminal segment (about 130 amino acids) followed by a collagen-like sequence (Maeda et al. 1996 supra). Adiponectin is a homotrimer that is similar in size and overall structure to complement protein C1q, with particularly high homology (about 65-70% homology) to C1q in the C-terminal globular domain. This globular domain (about 130 amino acids) is believed to be essential for the biological activity of adiponectin. The crystal structure of adiponectin revealed additional high structural similarity between this same globular domain and TNFalpha (about 60% homology).

Several recent studies suggest that adiponectin may be a hormone that links obesity, insulin resistance, and type 2 diabetes (Maeda et al. 2001 Nat. Med. 8:731-737; Yamauchi et al. 2001 Nat. Med. 7:941-946). APN may also be an important mediator between insulin resistance and atherosclerosis and thus could be an important target for future diabetes therapy (Brakenhielm et al. 2004 Proc. Natl. Acad. Sci. USA. 101: 2476-2481). Plasma APN concentrations are significantly lower in patients with obesity, type 2 diabetes and coronary artery disease compared to control subjects (Xu et al. 2003. J. Clin. Invest 112(1): 91-100).

The vascular action of insulin to stimulate endothelial production of nitric oxide (NO), leading to vasodilation and increased blood flow, is an important component of insulin-stimulated whole body glucose utilization (Berg et al. 2002 Trends Endocrinol. Metab. 13, 84-89), as well as of coronary artery disease and macroangiopathy (Weyer et al. 2001 J Clin Endocrinol Metab. 86:1930-1935). The decreased plasma APN concentrations in diabetes may be an diagnostic indicator of macroangiopathy (Weyer et al. 2001 supra; Matsubara et al. 2002 J Clin Endocrinol Metab. 87, 2764-2769).

However, the effects of adiponectin on angiogenesis have been conflicting; for example, Shibata et al. (J. Biol. Chem. 2004 279:28670-4) and Ouchi et al. (J. Biol. Chem. 2004 279:1304-9) reported that adiponectin stimulates angiogenesis while Rose et al. (Obes. Rev. 2004 5:153-65) and Brakenhielm et al. supra have reported that adiponectin inhibits angiogenesis. Most of the experimental data reported in these studies were obtained by in vitro assays using endothelial cells derived from large vessels. Mechanisms of action of adiponectin have not been elucidated in these studies.

In order to clarify the action of adiponectin in the angiogenic process, the studies disclosed herein were undertaken, specifically, to examine the role of APN in choroidal angiogenesis. The inventors discovered that APN expression was significantly lower in the choroids of laser-induced mouse model of CNV than in the choroids of control mice. Surprisingly, it was further discovered that the administration of recombinant APN or a fragment derived therefrom to the mice having laser-induced CNV reduced the size of CNV. Therefore, the present invention provides methods of inhibiting angiogenesis, in particular choroidal angiogenesis in vivo, by administering adiponectin or a functional fragment thereof. The invention further offers a new method of treating a condition or disease involving the process of angiogenesis, particularly wet type age related macular degeneration.

SUMMARY OF THE INVENTION

The present invention provides new methods of treating age related macular degeneration (AMD) by administering adiponectin (APN) or a functional fragment thereof. The invention is based on the discoveries that the level of APN expression is significantly lower in the choroids of the laser-induced mouse model of choroidal angiogenesis or choroidal neovascularization (CNV) than that of the control mice and that the administration of recombinant adiponectin (rAPN) or a fragment derived therefrom to the laser-induced mouse model reduced the size of CNV. These studies are believed to be the first to demonstrate that adiponectin is expressed in the choroids and can inhibit choroidal angiogenesis. Also these studies are the first to demonstrate that administration of intact adiponectin peptide or a fragment thereof can inhibit choroidal angiogenesis. Accordingly, the present invention provides methods for inhibiting angiogenesis with administration of adiponectin or a functional fragment thereof, to treat a condition or disease involving angiogenesis, particularly choroidal angiogenesis. Further, the present invention provides methods of inhibiting choroidal angiogenesis by up-regulating APN expression in vivo. The term, "up-regulation," as used herein, is intended to indicate that the expression of APN is increased either at transcriptional level or post-transcriptionally (e.g., RNA processing or translation). The inventive methods disclosed are particularly useful for treating wet type age related macular degeneration.

Adiponectin used in the studies disclosed herein is a mouse recombinant polypeptide of 30 kDa in length (obtained from BioVision Research Products, Mountain View, Calif.) or a smaller fragment derived from this protein. However, the amino acid sequences encoding adiponectin polypeptide are highly conserved among species (for example, the mouse adiponectin used herein shares about 83% amino acid identity with that of human) and thus adiponectin of other species including human, bovine, monkey and dog can also be used for the inventive methods (Fruebis et al. 2001 *PNAS* 98:2005-2050). Any "variant" functional forms (e.g., those having amino acid substitutions, insertions, deletions or those having modified amino acid residues while retaining its biological activity) of adiponectin protein of any species are also within the scope of this invention. Further, a fragment derived from intact adiponectin polypeptide of any species can also be used in the invention as long as the fragment retains its biological activity. These fragments are referred herein as a "functional fragment" or "functional biological fragment." An example of such a functional fragment is a 16 kDa peptide, a proteolytic cleavage product of 30 kDa adiponectin, which has been shown to have an enhanced fatty acid oxidation in mice (Fruebis et al. supra). The inventors have now shown that this 16 kDa fragment and a 18 mer peptide derived from the C-terminus (known as the globular domain) of the 30 kDa protein are as effective as the intact adiponectin protein in inhibiting CNV in the laser-treated mouse model. Functional "variants" of adiponectin or a fragment thereof include fusion proteins, for example, a functional fragment (e.g. 18 mer exemplified herein) of adiponectin fused to a heterologous sequence such as signal sequence, and peptides derived from the intact ADP having modified amino acid residues.

The peptide (18 mer) used herein to demonstrate that administration of exogenous adiponectin can inhibit choroidal angiogenesis or CNV consists of the amino acid sequence, LQVYGDGDHNGLYADNVN (SEQ ID NO:1). This sequence represents the region (amino acid residues 216-233) at the C-terminus of mouse adiponectin protein (total 247 amino acids in length). This region is commonly known as the globular domain, which is believed to be responsible for the biological activity of APN (Fruebis et al. 2001 *PNAS* 98:2005-2050). This region of APN is highly conserved among species. Thus, it is expected that any one of the corresponding sequences of human, bovine, and monkey adiponectin shown below or a larger peptide containing the core sequence shown below would exhibit similar inhibitory effects on CNV size as demonstrated herein.

```
Mouse    LQVYGDGDHNGLYADNVN   (SEQ ID NO: 1)
Human    LQVYGEGERNGLYADNDN   (SEQ ID NO: 2)
Bovine   LQVYEGENHNGVYADNVN   (SEQ ID NO: 3)
Monkey   LQVYGEGERNGLYADNDN   (SEQ ID NO: 4)
```

It is further predicted that a peptide consisting of the amino acid sequence of APN of any species, corresponding to the above mouse APN sequence, or a larger peptide containing such sequence would also have similar biological activity on choroidal angiogenesis.

The present invention also provides diagnostic kits to identify a subject for having wet type age related macular degeneration by measuring the level of APN expression (RNA or protein) in the serum of the subject.

BRIEF DESCRIPTION OF DRAWINGS

FIG. 1A shows ethidium bromide-stained bands for PCR products after UV exposure. Equal amounts of the total RNA (0.2 µg) were used to detect the mRNA levels of GAPDH, VEGF, βFGF, and APN. A band of similar intensity at 983 bp for GAPDH in lanes 1 and 2 indicates comparable amounts of RNA in each lane. Lane 3 is a sample from the laser-treated mice and lane 4 is a sample from the control, as shown in the panel under APN in FIG. 1A. APN expression in the laser-treated mice was significantly decreased as seen in lane 3 compared to lane 4. However, VEGF and βFGF mRNA levels were significantly increased in the laser-treated (lane 4) compared to the control (lane 3). FIG. 1B shows APN protein levels in the laser-treated and control mice in choroid (a) and serum (b). To detect APN in the choroid and serum samples Western blots were performed using antibodies specific for APN (Biovision Inc., Mountain View, Calif.). Choroids were collected from the mice, homogenized in solubilization buffer and the supernatants were analyzed on a SDS PAGE. Blood was collected from the mice and serum was separated from the blood for analysis. As seen in FIG. 1B, the expression of APN was decreased in the laser-treated (lane 1), day 3, compared to post lasered, day 7, lane 2 and control mice, non lasered (lane 3). The amount of protein loaded in each lane was 8 µg.

3A shows that there was 70% decrease in APN-injected (intravitreal) mice compared to control mice. FIG. 3B shows that there was 80% decrease (p<0.005) in the CNV size in the APN-injected (i.p.) mice compared to control mice. The values in each group were averaged from 80 laser spots. Lane 1 is the value obtained from the control and lane 2 is from the APN-injected mice.

FIG. 5 shows that VEGF expression is inhibited in the choroids of the laser-treated mice (lane 3) when APN was administered compared to the choroids of the laser-treated mice without the APN administration (lane 4). Lanes 1 and 2 are controls showing the levels of GAPDH mRNA.

FIG. 6 shows staining for adiponectin in neovascular complex in C57BL/6 mice on day 1 (A), day 3 (B), day 5 (C) and day 7 (D) after laser treatment. Monoclonal antibody for adiponectin (raised in rat, R &D systems, Minneapolis, Minn.) was used as primary antibody and goat anti-rat IgG FITC labeled (mouse Adsorbed, obtained from Serotec, Raleigh, N.C.) was used as the secondary antibody for adiponectin staining. Laser spots (CNV lesions) stained intensely (light area) for adiponectin in C57BL/6 at days 1 and 7 post-laser (A and D), very little staining was observed on day 5 (C). No staining for adiponectin was observed on day 3 (B).

DETAILED DESCRIPTION OF THE INVENTION

Figure 1A:
FIGS. 1A and 1B show the levels of GAPDH, VEGF, βFGF, and APN mRNA expression in post laser-treated and control mice.
Figure 1A:
Figure 1A:

In general the terms and phrases used herein have their art-recognized meaning, which can be found by reference to standard texts, journal references and contexts known to those skilled in the art. The following definitions are provided to clarify their specific use in the context of the invention.

An "effective amount" is an amount sufficient to effect beneficial or desired results including beneficial or desired clinical results. More specifically, an effective amount of APN or a functional variant or fragment thereof refers to an amount of the protein or polypeptide that is sufficient to exhibit a measurable improvement or protective effect in the subject. For example, one can monitor the local concentration of angiogenic factors as described in Yi et al. 1997 *Graefe's Arch. Clin. Exp. Opthamol.* 235:313-319 and Pierce et al. 1995 *PNAS* 92:905-909), or the size of CNV can be examined under fundus microscope (D'Amore et al. 1994 *Invest. Opthalmol. Vis. Sci.* 35:3874-3879). An effective amount for a given administration will vary depending on a variety of factors, i.e., severity of the disease, the age and weight of the subject, and route of administration etc. Beneficial results can include but are not limited to an improvement in an individual's vision or improvements in other disease conditions such as cancer, tumor, atherosclerosis, diabetic retinopathy, and corneal angiogenesis. An effective amount can be administered in one or more administrations by various routes of administration known in the art.

"Adiponectin" refers to a plasma protein secreted by adipocytes. Adiponectin is also referred to as Acrp30, adipoQ, or GBP28 and consists of 244 amino acids. An exemplary adiponectin used in the present invention is recombinant mouse adiponectin of about 30 kDa which is commercially available from Biovision Research Products (Mountain View, Calif.). Adiponectin useful for the invention can be any adiponectin of any species and can be a monomer or multimer (e.g., trimer). The sequences of adiponectin of various species are readily available in the art, for example, the sequences of human, mouse, bovine, monkey, and dog adiponectin can be found in the online Genbank database under accession numbers NP_004788, BAB22597, AAK58902, AAK92202 and AAL09702, respectively. The adiponectin can also be functional fragments derived from any intact adiponectin protein of any species.

Adiponectin useful for the invention further include adiponectin proteins or functional fragments thereof having certain modifications (e.g., glycosylation) and those having conservative amino acid substitutions, deletions or insertions in the adiponectin polypeptide without significantly changing the biological activity. These fragments are referred herein as "functional fragments" or "variants" of adiponectin. The functional fragments or variants are those molecules which are generally smaller than the intact APN and exhibit substantially equivalent to or enhanced biological activity of the intact adiponectin from which they are derived, as assayed by the art recognized methods (Maeda et al. 2001 *Nat. Med.* 8:731-737; Yamauchi et al. 2001 *Nat. Med.* 7:941-946). Also included herein are those adiponectin fragments or variants having at least 50% biological activity, preferably about 90% biological activity of the intact adiponectin.

Adiponectin activity can be measured by any art-recognized methods. For example, adiponectin activity is measured by its ability to inhibit proliferation of mouse myeloid cell line M1 as described in Yokota et al. *Blood* 2000 96:1723. In this assay, the ED50 for the effect is typically 1-7 μg/ml. Adiponectin activity can also be measured in vitro in a standard 72 hr BCE cell proliferation assay as well as in a cell migration assay using rVSM cells. For details of these assays, see Brakenhielm et al. *PNAS* 2004 101:2476-2481 and Cao et al. *PNAS* 2001 98:6390-6395.

The present inventors tested three different adiponectin peptides in the mouse model of choroidal angiogenesis or CNV. These include the full-length recombinant mouse adiponectin of about 30 kDa in size, a fragment of about 16 kDa described in Fruebis et al. (2005) supra, and a 18 mer synthetic peptide corresponds to the amino acid residues 216-233 of mouse adiponectin protein. In all cases, the biological effects observed were comparable, i.e., these peptides reduced the size of CNV similarly in the mouse model of CNV. These studies indicate that the inventive methods disclosed herein can be practiced with any fragment derived from the full-length adiponectin of any species as long as the fragment contains the 18 amino acids correspond to the sequence given in SEQ ID NO: 1.

As used herein a conservative substitution refers to the substitution of one amino acid for another having similar size and/or charge. Groups of amino acids known to be equivalent in the art include, for example: (a) Ala, Ser, Thr, Pro, and Gly; (b) Asn, Asp, Glu, and Gln; (c) His, Arg, and Lys; (d) Met, Ile, and Val; and (e) Phe, Tyr, and Trp. Adiponectin variants include those having 1-25 conservative amino acid substitutions which retain the biological function.

The adiponectin peptide useful for the invention can be a product purified from a biological material (e.g., blood), synthesized by art-known chemical methods or prepared recombinantly by art-known methodology. For protocols, see Ausubel et al. (Eds.) (1995) *Current Protocols in Molecular Biology*, Greene Publishing and Wiley Interscience, New York; and Metzger et al. (1988) *Nature*, 334: 31-36. Many useful vectors for expression in bacteria, yeast, fungal, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Polymerase Chain Reaction (PCR) is a repetitive, enzymatic, primed synthesis of a nucleic acid sequence. This procedure is well known and commonly used by those skilled in this art [see Mullis, U.S. Pat. Nos. 4,683,195, 4,683,202, and 4,800,159; Saiki et al. (1985) *Science* 230:1350-1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase, result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art. Various improved methods for conducting PCR are known in the art.

Those skilled in the art can clone and produce adiponectin protein or a functional fragment thereof including adiponectin variants having a deletion, insertion or substitution(s) by employing various methods well known in the art. A wide variety of restriction enzymes which are suitable for generating fragments from larger nucleic acid molecules are well known. In addition, it is well known that Bal31 exonuclease can be conveniently used for time-controlled limited digestion of DNA, which is useful for generating various deletions. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258:13006-13512). By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original molecule. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) Genetika 18(3):349-59; Shortle, D, DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

Adiponectin can be formulated in a manner suitable for administration of a protein or peptide to a subject, particularly human, preferably in a form for parenteral administration via routes such as subretinal, intraperitoneal (i.p.), intravenous (i.v.), subcutaneous (s.c.), intradermal (i.d.) or transdermal. Other preparations are also envisaged in which adiponectin is administered via the oral, rectal, vaginal, intravesical, intraventricular, intracerebral or other routes known to those in the art. The adiponectin preparation can also be formulated in a delivery vehicle such as liposomes to maximize it effects. Methods for liposome delivery of proteins or peptides are well known in the art.

The adiponectin preparation is typically formulated in aqueous solution containing buffers for stabilization at a physiologically acceptable ionic strength, and optionally with suitable antiseptic, antifoaming, anti-precipitation and other stabilizing agents known to those skilled in the art to be suitable for pharmaceutical formulation of proteins or peptides for administration to mammals, particularly humans.

Adiponectin can also be administered to a subject in an appropriate dosage form known in the art to be suitable for pharmaceutical formulation of proteins or peptides for administration to mammals, in particular humans. Examples include, but are not limited to, oral delivery forms (tablet, capsule, lozenge, or the like form, or any liquid form such as syrups, aqueous solutions, emulsion and the like, capable of protecting the therapeutic protein from degradation prior to eliciting an effect), transdermal delivery forms (patches and bandages), topical dosage forms (lotion, spray, ointment, paste, eye drops, cream, gel, etc.), suppository delivery forms, and transmucosal delivery forms (depositories).

Adiponectin of this invention and functional variants and fragments thereof can be combined with other components known in the art to provide benefit for treatment of diseases, disorders or conditions of the eye or prevention of such diseases, disorders or conditions.

Pharmaceutically acceptable salts include, but are not limited to, the acid addition salts (formed with free amino groups of a peptide) which are formed with inorganic acids, e.g., hydrochloric acid or phosphoric acids; and organic acids, e.g., acetic, oxalic, tartaric or maleic acid. Salts formed with the free carboxyl or phosphate groups can also be derived from inorganic bases, e.g., sodium, potassium, ammonium, calcium, or ferric hydroxides, organic bases, e.g., isopropylamine, trimethylamine, 2-ethylamino ethanol, histidine, procaine, or cationic lipids.

The studies disclosed herein were designed to investigate the role of adiponectin (APN) in choroidal angiogenesis or CNV. The studies demonstrate that adiponectin is expressed at a significant level in the choroids of normal mice and that the level of APN expression is reduced in the laser-induced mouse model of CNV compared to the control mice. The details of these studies are provided in the following examples.

EXAMPLES

Animals

C57BL/6 mice 4-6 weeks old were purchased from the Jackson Laboratory (Bar Harbor, Me.). This study was approved by the Institutional Animal Care and Use Committee (IACUC), University of Louisville, Louisville, Ky.

RT-PCR Analysis

Ten laser spots were placed in each eye of C57BL/6 mice as described below. Animals from each group (n=10/each time point) were sacrificed at days 1, 3, 5, and 7 post-laser treatment, RPE-choroid-scleral tissues harvested from the enucleated eyes were pooled separately for each time point and without laser treatment (control), and total RNA was prepared using SV Total RNA Isolation kit (Promega, Madison, Wis.). Equal amounts of the total RNA (0.2 µg) were used to detect the mRNA levels of GAPDH, VEGF, β-FGF and APN by RT-PCR using the reagents purchased from Applied Biosystems. The sense and antisense oligonucleotide primers were synthesized at Integrated DNA Technologies, and PCR used 30 cycles. The negative controls consisted of omission of RNA or reverse transcriptase in the reaction mixture. PCR products were analyzed on a 2% agarose gel and were examined by using the Molecular Analyst/PC program (Bio-Rad). RT-PCR was conducted using the following primers: GAPDH (forward (F), 5'-TGAAGGTCGGTGTGAACG-GATTTGGC-3', SEQ ID NO; 5; reverse (R), 5'-CATGTAG-GCCATGAGGTCCACCAC-3', SEQ ID NO: 6); VEGF (F, 5'-GCGGGCTGCCTCGCAGTC-3', SEQ ID NO: 7; R, 5'-TCACCGCCTTGGCTTGTCAC-3', SEQ ID NO: 8); β-FGF (F, 5'-AGCGGCTCTACTGCAAGAAC-3', SEQ ID NO: 9; R, 5'-TCGTTTCAGTGCCACATACC-3', SEQ ID NO: 10); TGF-β2 (F, 5'-CCAAAGACTTAACATCTC-CCACC-3', SEQ ID NO: 11; R, 5'-GTTCGATCTTGGGCG-TATTTC-3', SEQ ID NO: 12); APN (F, 5'-ATGGGC-TATGGGTAGTTGCAGTCA-3', SEQ ID NO: 13; R, 5'-TAGCTTCATGCTTTGGGTCCTCCA-3', SEQ ID NO: 14)

Figure 1B:
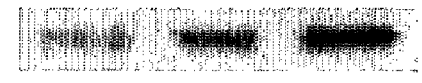

As shown in FIGS. 1A and 1B, the expression of APN was low in laser-treated mice compared to non-laser-treated mice. The expression of VEGF, and βFGF in the laser-treated mice was similar on days 1 and 7; however, the expression of the growth factors was significantly higher in laser-treated mice (see lane 4) compared to non-laser-treated mice (FIG. 1A). These results are consistent with the results of Western blot analysis shown in FIG. 1B.

Western Blot Analysis

RPE-choroid-scleral tissues were homogenized and solubilized in ice cold PBS (2.0 ml/eye) containing protease inhibitors, phenylmethylsulfonyl fluoride (PMSF, 1 µg/ml), aprotinin (1 µg/ml), and EDTA (1 mM). The homogenates were centrifuged at 18,000 g at 4° C. for 30 minutes. The protein contents of the supernatants were determined by the Bradford method. After sodium dodecyl sulfate polyacrylamide gel electrophoresis (SDS-PAGE) on 10% linear slab gel, under reducing conditions, separated proteins were transferred to a polyvinylidene fluoride (PVDF) membrane using a semidry electrophoretic transfer cell (Trans-Blot; Bio-Rad, Richmond, Calif.). Blots were stained at room temperature with a 1:300 dilution of IgG fraction of anti-mouse APN for overnight at 4° C. Control blots were treated with the same dilution of normal goat serum. After washing and incubation with horseradish peroxidase-conjugated secondary antibody (1:10,000 dilution), blots were developed using the enhanced chemiluminescence Western blot analysis detection system (ECL Plus; Amersham Pharmacia Biotech, Arlington Heights, Ill.). Quantification of APN was accomplished by densitometry (Alpha Imager 2200; Alpha Innotech; San Leandro, Calif.).

Immunohistochemical Studies

To investigate the presence of APN in the eyes of C57BL/6 mice, the immunohistochemistry was carried out as described below using paraffin embedded mice eyes. The animals were sacrificed and the eyes were processed for paraffin sectioning. The slides were rinsed and incubated for 10 minutes with EDTA to unmask the antigenic markers for adiponectin. Again, the slides were rinsed and incubated for 20 minutes with blocking solution (5% goat serum+5% BSA in PBS). After rinsing, the slides were incubated with anti-mouse APN (primary antibody, Biovision Inc., CA) at 4° C. overnight. The slides were again rinsed and incubated for 60 minutes with Cy3 labeled goat anti-mouse antibody (secondary antibody, Serotec Inc., NC). A final rinsing was followed by mounting with Aqua-Mount (Lerner Laboratories, PA). Sections were examined under fluorescence microscope (Zeiss).

Figure 2:
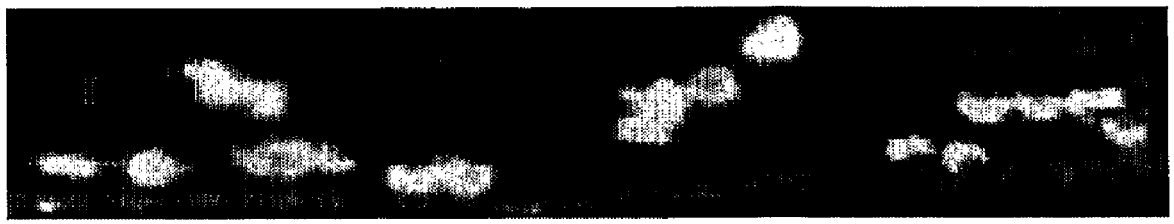
FIG. 2 shows the results of immunohistological analyses performed using paraffin embedded rat eyes. Adiponectin antibody (Biovision Inc., Mountain View, Calif.) and Cy3 labeled goat anti-mouse antibody (Serotec Inc., Raleigh, N.C.) were used as primary and secondary antibodies. The slides were mounted with Aqua-Mount (Lerner Laboratories, Pittsburgh, Pa.). Sections were examined under a fluorescence microscope (Zeiss). The figure shows staining in the choroid (light area) but no staining in the retina, sclera or lens.
Figure 3A:
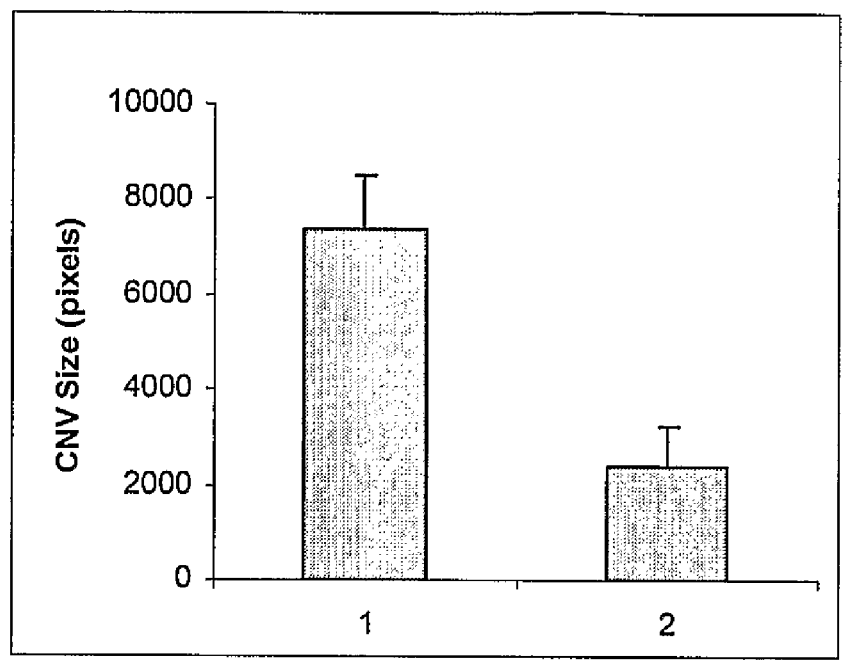
FIGS. 3A and 3B illustrate that the size of CNV was reduced by APN administration in the laser-induced mouse model of CNV. The size of CNV was measured after APN administration, either intraperitoneally (i.p.) or intravitreally, in the laser-induced and control mice. The control mice were injected with PBS, i.p. or intravitreal. The CNV size was measured in pixels by using Image Pro-Plus software. FIG.
Figure 3B:
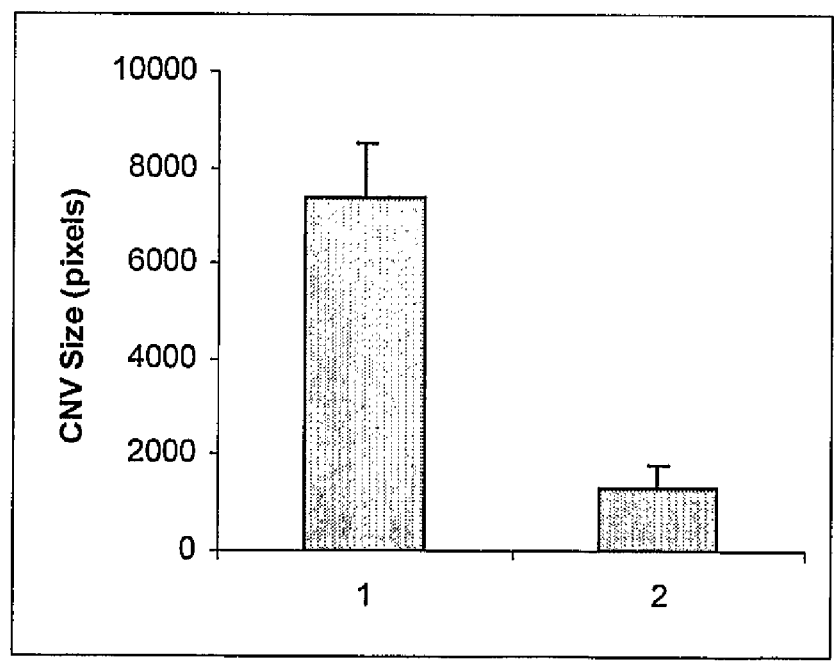
Figure 4A:
FIGS. 4A and 4B show that the neovascular complex was significantly smaller after APN was administered to the laser-induced C57BL/6 mice compared to the control. The mice were anesthetized and perfused with 1 ml of PBS containing 50 mg/ml fluorescein-labeled dextran. The flat mounts were stained for elastin by using elastin antibody and Cy3-conjugated secondary antibody, and were examined by confocal microscope. Confocal micrograph of the neovascular complex in C57BL/6 mice shows the new vessels. Exposed Bruch's membrane with elastin stained red; otherwise, intact RPE (Retinal pigment epithelium) obscures Bruch's membrane. Neovascular complex was significantly inhibited in the laser spots of C57BL/6 mice treated with APN i.p. compared to the control, FIG. 4B compared to FIG. 4A. Similar results were obtained with intravitreal injection of APN, FIG. 4 C compared to FIG. 4D (control).
Figure 4B:
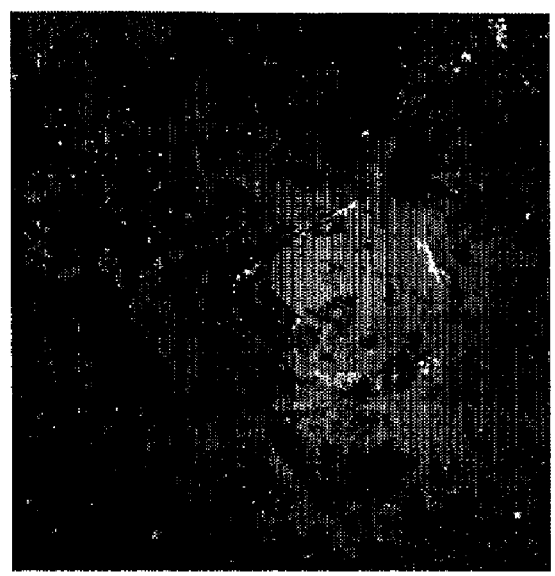
Figure 4C:
Figure 4D:
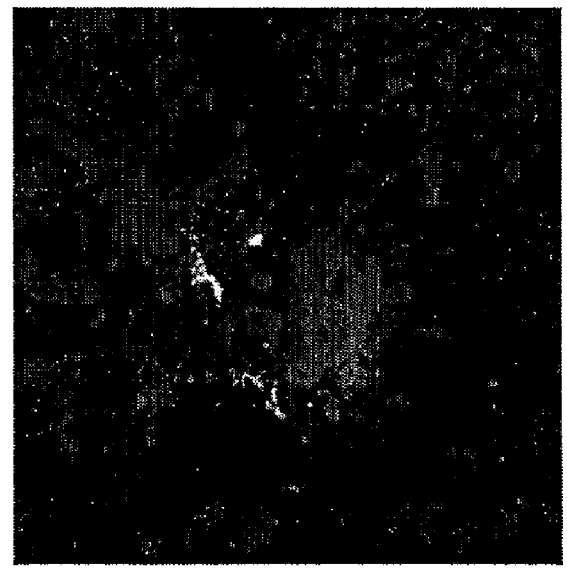

As seen in FIG. 2, only choroid, cornea, iris, and colliery body were stained in the eye. In particular, choroidal endothelial cells were densely stained.

Induction of CNV in Mice/Adiponectin Treatment

Animals (C57BL/6 mice) were divided into 3 groups. CNV was induced by laser photocoagulation in group 1 (n=5) with the krypton red laser (50 μm spot size; 0.05 s duration; 250 mW), as previously described (Bora et al. 2003 Proc. Natl. Acad. Sci. USA 100:2679-2685; Bora et al. 2005 J. Immunol. 174:491-497) and no APN was administered to these mice. Three laser spots were placed in each eye close to the optic nerve. In group 2 (n=5), the mice were treated, i.p., with 25 μg of rAPN, one day before laser photocoagulation and every day after laser treatment until day 6. Group 3 animals received subretinal injections on days 0, 1, and 3 in one eye, the other eye received PBS as control. All the experiments were repeated three times.

Peptide Administration

We injected 50 μg peptide NH2-LQVYGDGDHNGLY-ADNVN-COOH (SEQ ID NO: 1, synthesized at Peptide Biochemical Research Inc. Seattle, USA; dissolved in PBS) intraperitoneally (i.p.) to mice (n=5) as well as intravitreally (i-vit.). Six i.p. injections were given, one preceding laser treatment and five following the laser treatment. Control group was given sterile PBS. One group (n=5) was photocoagulated on day 0 and on day 1 a single 30 μg i-vit. injection was given. All the experiments were repeated three times. Mice were sacrificed following perfusion with FITC dextran on day 7 and eyes removed and fixed in formaldehyde. Choroidal-scleral flat mounts were prepared and processed for immunostaining. Laser confocal micrographs were used to measure the size of CNV by Image-Pro-Plus software (Media Cybernetics, Inc. Silver Spring, Md.).

Measurement of CNV

Seven days after laser treatment, the eyes of all animals were perfused with 1 ml of PBS containing 50 mg/ml fluorescein-labeled dextran (FITC-dextran; average molecular mass, $2\times10^6$; Sigma-Aldrich) and the animals were sacrificed. The eyes were harvested and fixed in 10% phosphate-buffered formalin, and retinal pigment epithelium (RPE)-choroid-scleral flat mounts were prepared as previously described (Bora et al. 2003 supra; Bora et al. 2005 supra.). RPE-choroid-scleral flat mounts were stained for elastin using a mAb specific for elastin (1.0 mg/ml; 1/2000 dilution; Sigma-Aldrich) followed by a Cy3-labeled secondary Ab (1.0 mg/ml; 1/2000 dilution; Sigma-Aldrich). The incidence and the size of CNV were determined by confocal microscopy. The size of the CNV complex was graded by morphometric analysis of the images (MetaMorph Image Analysis software package; Universal Imaging) obtained from confocal microscopy.

Figure 7A:
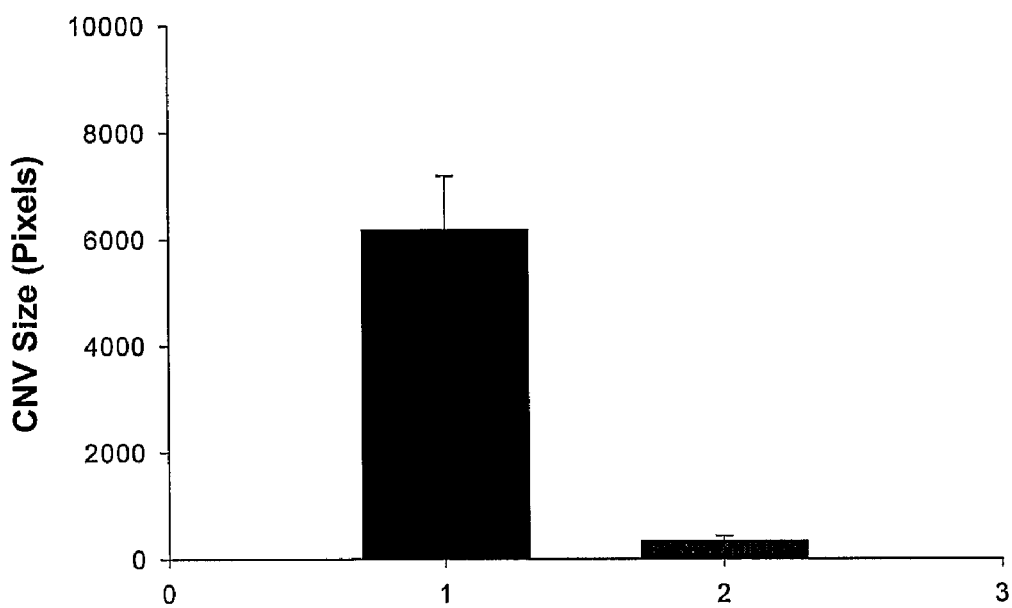
FIG. 7 illustrates the effect of a peptide (SEQ ID NO:1) administration on CNV size. This 18 mer peptide was designed from the region of adiponectin molecule which is known to be essential for its biological activity. The peptide was injected i.p. and i-vit from day 0 to day 5. Six i.p. injections (50 μg/mouse) were given daily to mice, one preceding laser treatment and five following laser treatment. A single dose of peptide (30 μg/ul) was administered intravitreally (i-vit) a day after laser treatment. Control mice were administered sterile PBS. Mice were sacrificed on day 7 and choroidal-scleral flat mounts were prepared and processed for immunostaining. The flat mounts were stained for elastin by using elastin Ab and Cy3-conjugated secondary Ab, and were examined by confocal microscope. Confocal micrograph of the neovascular complex in C57BL/6 mice shows new vessels. A significant reduction (p<0.005) in CNV size in peptide treated groups, both by i.p. injection, FIG. 7A and i-vit injection, FIG. 7B, compared to the control, was observed. Similarly, the neovascular complex was significantly inhibited in the laser spots of C57BL/6 mice when treated with the peptide regardless of the mode of administration, as can be seen in FIG. 7F compared to 7E (intravitreal injection) and FIG. 7C compared to 7D (i.p. injection).
FIGS. 7C-7F are examples of confocal images.
Figure 7B:
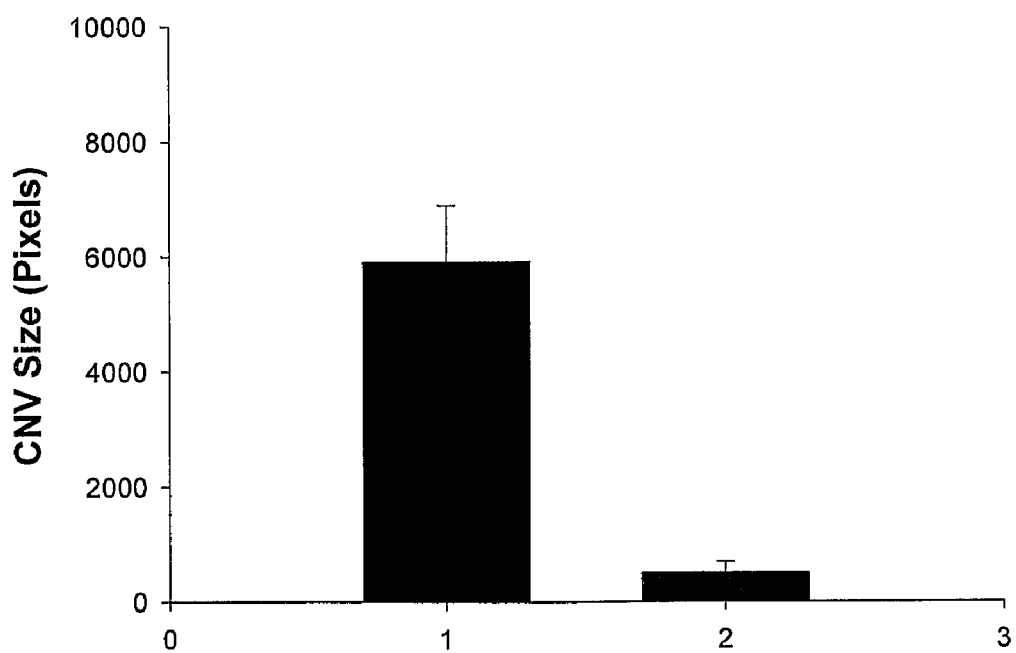

There was about 70-80% decrease in the CNV complex size in the mice which had been injected i.p or i-vit. with rAPN or the 18 mer peptide, compared to the control mice. FIGS. 7A and 7B show the results obtained with the 18 mer peptide injection, either i.p or i-vit. The values in each group were averaged from 80 laser spots (FIGS. 7A and 7B). In general, the reduction in CNV size was more significant when the rAPN or the peptide was administered intraperitoneally (~80%) than intravitreally (~70%). The confocal images shown herein represent the images used to calculate the size (FIGS. 7B-7D).

In summary, the studies described above show that APN is expressed in choroid, cornea, iris, and cilliary body of the eye of normal mice. These studies further showed that APN expression was significantly lower in the choroids of lasered mice compared to non-lasered mice. When 25 μg of recombinant APN (dissolved in PBS) or 50 μg of the 18 mer peptide derived from the globular region of APN was injected to the lasered mice intraperitoneally, the size of the CNV was reduced by 80% in APN treated mice compared to the control mice which did not receive adiponectin. Similarly, the size of the CNV was reduced by 70% in APN treated mice compared to control mice when 5 μg recombinant APN or a peptide derived therefrom was injected subretinally into the eye of the lasered mice. In both instances, adiponectin was dissolved in PBS buffer and the control animals received PBS only. These results indicate that APN is a direct endogenous angiogenesis inhibitor and can be used in the treatment of CNV or AMD.

These studies represent the first testing of APN as an anti-angiogenesis protein in an in vivo CNV model. We have shown herein that APN is expressed in the choroid of normal mice in high amounts and that the expression of APN is significantly reduced in laser spots (i.e. CNV spots) compared to non-laser-treated choroids. Based on these results, we believe that the decreased level of APN in the choroids facilitates the initiation of the angiogenesis process along with elevated levels of VEGF and βFGF in the laser-treated mice. This is consistent with the results shown in FIG. 5 where the APN administration to the choroids of the laser-treated mice inhibited VEGF expression. These results indicate that a combination of APN and any agents capable of inhibiting VEGF and/or βFGF action would be beneficial (additive or synergistic) to treat a condition or disease involving angiogenesis. These findings can also be employed in the diagnosis of the wet type of macular degeneration in a subject since the level of expression of APN in the choroids of such subjects would be diminished compared to normal subjects. It is predicted that the serum concentration of APN in a subject suspected of having AMD is lower than that in control subjects. Accordingly, the present invention provides the kit for diagnosing wet type AMD by measuring the level of APN expression in a subject by Western blot (or ELISA), or RT-PCR (or Northern blot).

The studies described herein indicate that APN can inhibit choroid neovascularization when present in the choroids at sufficient levels, i.e. APN acts as anti-angiogenic agent. Particularly, these results demonstrate that introduction of exogenous APN inhibits CNV in an in vivo mouse model. Therefore, the present invention provides a new method of treating age related macular degeneration by inhibiting choroidal angiogenesis or CNV by administering adiponectin or a functional fragment derived therefrom. These results further indicate that a composition which is capable of increasing APN expression in vivo would be useful to inhibit angiogenesis. One example of such composition is thiazolidinediones which are known to increase APN in circulation. Currently, thiazolidinediones are used in combination with diet and exercise to treat type 2 diabetes. Another example is endothelin-1 (ET-1, Sigma Inc. St. Louis, Mo.) which is shown to increase APN secretion acutely from adipocyte in vitro. Accordingly, those skilled in the art can use these compounds to increase APN expression and/or secretion in vivo.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the invention is to be limited only to the claims except as precluded by the prior art. Moreover, the invention as disclosed herein, may be suitably practiced in the absence of the specific elements which are disclosed herein.

All references cited in the present application are incorporated in their entirety herein by reference. In cases of any inconsistency in definitions of terms and phrases used herein, in any references incorporated herein, the definitions in this disclosure dominate. Certain references are incorporated herein for example to provide sources of APN, sequences of APN, and methods for assaying the biological function of APN.

When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known and available in the art prior to Applicants' invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, reagents, solid substrates, synthetic methods, purification methods, and analytical methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis, additional methods of analysis and additional uses of the invention.

We claim:

1. A method of inhibiting angiogenesis in a cell or tissue in vivo by administering to the cell or tissue an effective amount of an 18 mer adiponectin fragment consisting of the amino acid sequence selected from the group consisting of SEQ ID NO:1, SEQ ID NO:2, SEQ ID NO:3, and SEQ ID NO:4.

2. The method of claim 1 wherein the cell or tissue is that of the eye.

3. The method of claim 2 wherein the adiponectin fragment is administered intravitreally.

4. The method of claim 1 wherein the adiponectin fragment is administered intraperitoneally.

5. The method of claim 1 wherein the cell or tissue is not that of cancer.

6. The method of claim 1 wherein the adiponectin fragment is a peptide consisting of the amino acid sequence set forth in SEQ ID NO:1.

7. The method of claim 1 wherein the effective amount of the adiponectin fragment is part of a pharmaceutical composition.

8. A method of treating wet type age related macular degeneration in a subject by administering to the subject an effective amount of an 18 mer adiponectin fragment consisting of the amino acid sequence selected from the group consisting of SEQ ID NO:1, SEQ ID NO:2, SEQ ID NO:3, and SEQ ID NO:4.

9. The method of claim 8 wherein the adiponectin fragment is administered intraperitoneally.

10. The method of claim 8 wherein the adiponectin fragment is administered intravitreally.

11. The method of claim 8 wherein the adiponectin fragment is a peptide consisting of the sequence as set forth in SEQ ID NO:1.

12. The method of claim 8 wherein said administration of an effective amount of the adiponectin fragment inhibits choroidal angiogenesis or choroidal neovascularization in the subject.

* * * * *